United States Patent
Matsuzaki et al.

(10) Patent No.: US 8,905,636 B2
(45) Date of Patent: Dec. 9, 2014

(54) X-RAY DIAGNOSTIC APPARATUS

(71) Applicants: Takeo Matsuzaki, Nasushiobara (JP); Yasunori Goto, Shioya-gun (JP); Rie Ochiai, Nasushiobara (JP)

(72) Inventors: Takeo Matsuzaki, Nasushiobara (JP); Yasunori Goto, Shioya-gun (JP); Rie Ochiai, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 137 days.

(21) Appl. No.: 13/731,462

(22) Filed: Dec. 31, 2012

(65) Prior Publication Data
US 2013/0121466 A1 May 16, 2013

Related U.S. Application Data

(63) Continuation of application No. PCT/JP2012/050293, filed on Jan. 10, 2012.

(30) Foreign Application Priority Data

Jan. 11, 2011 (JP) ................................. 2011-003438
Jan. 9, 2012 (JP) ................................. 2012-001736

(51) Int. Cl.
  *G01T 1/00* (2006.01)
  *A61B 6/00* (2006.01)

(52) U.S. Cl.
  CPC ............... *A61B 6/586* (2013.01); *A61B 6/4233* (2013.01)
  USPC .......................................... 378/207; 378/116

(58) Field of Classification Search
  USPC .......................................... 378/98.8, 207, 116
  See application file for complete search history.

(56) References Cited

U.S. PATENT DOCUMENTS

| 4,905,265 | A  | * | 2/1990 | Cox et al. ..................... 378/98.8 |
| 8,393,789 | B2 | * | 3/2013 | Enomoto ........................ 378/207 |
| 2006/0054846 | A1 | * | 3/2006 | Satoh et al. ................... 250/587 |
| 2009/0010391 | A1 |   | 1/2009 | Kito et al. |
| 2011/0102184 | A1 |   | 5/2011 | Kito et al. |

FOREIGN PATENT DOCUMENTS

| JP | 8-266532 A | 10/1996 |
| JP | 2002-148211 A | 5/2002 |
| JP | 2003-042976 A | 2/2003 |
| JP | 2005-308600 A | 11/2005 |
| JP | 2006-84259 A | 3/2006 |
| JP | 2007-20925 A | 2/2007 |
| JP | 2007-121010 A | 5/2007 |
| JP | 2009-34484 A | 2/2009 |
| JP | 2010-82426 A | 4/2010 |

* cited by examiner

OTHER PUBLICATIONS

Combined International Search Report and Written Opinion issued Jun. 5, 2012 in PCT/JP2012/050293 filed Jan. 10, 2012 (with English translation of Category of Cited Documents).

*Primary Examiner* — Hoon Song
(74) *Attorney, Agent, or Firm* — Oblon, Spivak, McClelland, Maier & Neustadt, L.L.P.

(57) ABSTRACT

According to one embodiment, an end-of-life detection unit in an X-ray diagnostic apparatus is configured to detect an end of life of a detector on the basis of an output value in an X-ray image, and includes: a luminance-level-value computation unit configured to calculate an amount of X-ray irradiation of the detector on the basis of the output value in an area of interest which is set on any one of the X-ray image and the detector; an irradiation-amount accumulation unit configured to calculate an accumulated amount of irradiation in the area of interest by adding the amount of X-ray irradiation calculated by the luminance-level-value computation unit to a previous amount of X-ray irradiation in the area of interest; and an end-of-life judgment unit configured to make a judgment on the end of life of the detector on the basis of the accumulated amount of irradiation.

20 Claims, 11 Drawing Sheets

X-RAY DIAGNOSTIC APPARATUS

CROSS-REFERENCE TO THE RELATED APPLICATION

This application is based on and claims the benefit of priority from Japanese Patent Application No. 2011-003438, filed on 11 Jan. 2011, and Japanese Patent Application No. 2012-001736, filed on 9 Jan. 2012; the entire contents of which are incorporated herein by reference.

FIELD

Embodiments of the present invention relate to an X-ray diagnostic apparatus and to an X-ray diagnostic apparatus capable of figuring out its detector's condition in terms of sensitivity deterioration, the detector being configured to detect an X ray applied to a patient.

BACKGROUND

As radiation detectors for obtaining a radiograph of a subject, ones combining an image intensifier (hereinafter, referred to as "I.I.") with a pickup tube or a solid-state image sensing device (e.g. a charge coupled device: hereinafter, referred to as "CCD") have heretofore been used. These are configured to convert information on X rays transmitted through a subject into optical information, take this optical information into a television camera, and display it on a television monitor as an image or print it onto a film.

For these radiation detectors combining an I.I. with a pickup tube or a CCD, there has been a great need for the detection of smaller impaired parts and subtler lesions. As a new radiation detector to fulfill this need, a flat panel detector (hereinafter, referred to as "FPD") making use of semiconductor techniques has been developed. This FPD is a semiconductor array formed in such a way that switching elements and capacitance formed on a glass substrate, for example is covered with a photoconductive film configured to convert radiation into charge. The FPD has features such as high resolution, light-weight and compact, and small image distortion.

As described, I.I.s and FPDs are available as detectors for obtaining a radiograph of a subject (see Japanese Patent Application Publication No. 2009-75951, for example).

As for the life of such a detector, the total accumulated amount of X-ray irradiation at the end of life is found when the detector is commercialized. By assuming the frequency of use of the detector, the durable term thereof is calculated. The user figures out the life of the detector on the basis of this durable term.

However, clinical settings in which an X-ray diagnostic apparatus equipped with the detector is installed differ from one another in terms of for what application and how frequently the apparatus is used. Thus, the assumed durable term mentioned above is inevitably inaccurate in practical use. Moreover, at present, no specific method has been established for notifying the operator of the end of life of the detector that is attributable to sensitivity deterioration by X-ray irradiation.

DETAILED DESCRIPTION

Figure 1:
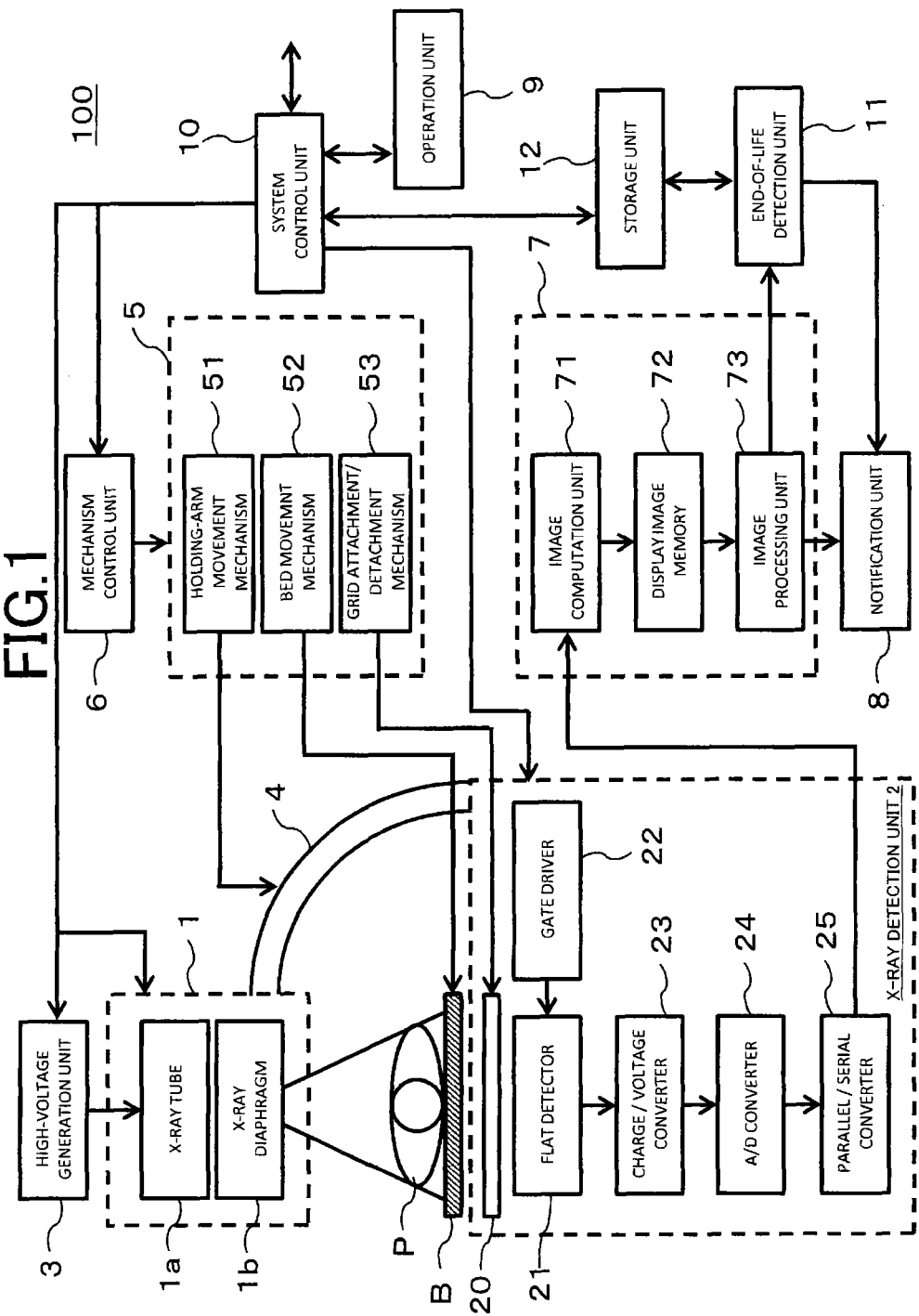
FIG. 1 is an overall diagram showing a schematic configuration of an X-ray diagnostic apparatus in a first embodiment.

According to an embodiment, an X-ray diagnostic apparatus includes: an X-ray generation unit configured to generate an X ray with which a subject is to be irradiated; an X-ray detection unit including a detector and configured to create X-ray transmission information, the detector being configured to detect the X ray transmitted through the subject; an image creation unit configured to create an X-ray image on the basis of the X-ray transmission information; and an end-of-life detection unit configured to detect an end of life of the detector on the basis of an output value in the X-ray image. The end-of-life detection unit includes: a luminance-level-value computation unit configured to calculate an amount of X-ray irradiation of the detector on the basis of the output value in an area of interest which is set on any one of the X-ray image and the detector; an irradiation-amount accumulation unit configured to calculate an accumulated amount of irradiation in the area of interest by adding the amount of X-ray irradiation calculated by the luminance-level-value computation unit to a previous amount of X-ray irradiation in the area of interest; and an end-of-life judgment unit configured to make a judgment on the end of life of the detector on the basis of the accumulated amount of irradiation.

According to another embodiment, An X-ray diagnostic apparatus comprising: an X-ray generation unit configured to generate an X ray with which a subject is to be irradiated; an X-ray detection unit including a detector and configured to create X-ray transmission information, the detector being configured to detect the X ray transmitted through the subject; an image creation unit configured to create an X-ray image on the basis of the X-ray transmission information; and an end-of-life detection unit configured to detect an end of life of the detector on the basis of a pixel value in the X-ray image, wherein the end-of-life detection unit includes a luminance-level-value computation unit configured to calculate the pixel value in an area of interest which is set on any one of the X-ray image and the detector, a pixel-value accumulation unit configured to calculate an accumulated pixel value in the area of interest by adding the pixel value calculated by the luminance-level-value computation unit to a previous pixel value in the area of interest, and an end-of-life judgment unit configured to make a judgment on the end of life of the detector on the basis of the accumulated pixel value.

According to another embodiment, An X-ray diagnostic apparatus comprising: an X-ray generation device including an X-ray generation unit configured to generate an X ray with which a subject is to be irradiated, and a system control unit configured to control the X-ray generation unit; and an image collection device including an X-ray detection unit including a detector and configured to create X-ray transmission information, the detector being configured to detect the X ray transmitted through the subject, an image creation unit configured to create an X-ray image on the basis of the X-ray transmission information, a luminance-level-value computation unit configured to calculate an amount of X-ray irradiation of the detector on the basis of the output value in an area of interest which is set on any one of the X-ray image and the detector, an irradiation-amount accumulation unit configured to calculate an accumulated amount of irradiation in the area of interest by adding the amount of X-ray irradiation calculated by the luminance-level-value computation unit to a previous amount of X-ray irradiation in the area of interest, and an end-of-life judgment unit configured to make a judgment on an end of life of the detector on the basis of the accumulated amount of irradiation.

Various Embodiments will be described hereinafter with reference to the accompanying drawings.

(First Embodiment)

In a first embodiment, a stationary X-ray diagnostic apparatus 100 incorporating a flat detector configured to receive irradiation of X rays is used to describe an example of the calculation of the amount of X-ray irradiation of the flat detector.

First, the configuration of the X-ray diagnostic apparatus 100 in the first embodiment will be described using FIG. 1. FIG. 1 is an overall diagram showing a schematic configuration of the X-ray diagnostic apparatus 100 in the first embodiment.

The X-ray diagnostic apparatus 100 includes: an X-ray generation unit 1 configured to irradiate a subject P with X rays; and an X-ray detection unit 2 configured to detect two-dimensionally the X-rays transmitted through the subject P. The X-ray diagnostic apparatus 100 also includes: a high-voltage generation unit 3 configured to generate a high voltage that is necessary for the X-ray irradiation in the X-ray generation unit 1; a holding arm 4 configured as a C arm, for example, to hold the X-ray generation unit 1 and the X-ray detection unit 2; and a bed (top plate) B on which the subject P lies.

The X-ray diagnostic apparatus 100 also includes: a mechanism unit 5 configured to move the holding arm 4 and the bed (top plate) B, attach and detach a grid 20 that is designed to be attached to a later-described flat detector 21 of the X-ray detection unit 2, and so on; a mechanism control unit 6 configured to control mechanisms of the mechanism unit 5; and an image creation unit 7 configured to create an image out of X-ray transmission information detected by the X-ray detection unit 2 and to store it.

The X-ray diagnostic apparatus 100 further includes: a notification unit 8 configured to display X-ray image data created and stored by the image creation unit 7; an operation unit 9 which the apparatus operator (hereinafter, referred to as "operator") uses to give various instructions to the X-ray diagnostic apparatus 100; and a system control unit 10 configured to control each of the above-described units of the X-ray diagnostic apparatus 100. In addition to these, the X-ray diagnostic apparatus 100 includes an end-of-life detection unit 11 configured to detect the end of life of the flat detector 21, and a storage unit 12.

The X-ray generation unit 1 includes: an X-ray tube 1*a* configured to irradiate the subject P with X rays; and an X-ray diaphragm 1*b* configured to focus the X rays emitted from the X-ray tube 1*a* on the subject P. The X-ray tube 1*a* is a vacuum tube for generating X rays, where the X rays are generated by accelerating electrons, which are emitted from a cathode (filament), with a high voltage and causing them to collide with a tungsten anode. The X-ray diaphragm 1*b*, on the other hand, is located between the X-ray tube 1*a* and the subject P and has a function of narrowing the flux of X rays emitted from the X-ray tube 1*a* into the size of the imaging area.

On the other hand, the X-ray detection unit 2 configured to detect X rays upon irradiation of the X rays includes the grid 20, the flat detector 21, a gate driver 22, a charge/voltage converter 23, an A/D converter 24, and a parallel/serial converter 25.

The grid 20 is configured to prevent the flat detector 21 from receiving scattered X rays produced in the subject P during the X-ray irradiation. Thus, in the X-ray detection unit 2, the grid 20 is disposed at such a position as to face the bed (top plate) B.

The flat detector 21 is configured to convert the X rays transmitted through the subject P into charges and store them. The flat detector 21 is formed by arranging small detection elements two-dimensionally in a column direction and a line direction. Each of these detection elements is configured to sense X rays, produce a charge based on the amount of incident X rays, and send this charge to the charge/voltage converter 23.

The gate driver 22 is configured to supply a drive voltage to the gate terminals of TFTs so as to read out the charges stored in the flat detector 21 as X-ray image signals. The charge/voltage converter 23 is configured to convert the charges read out from the flat detector 21 into voltages. The A/D converter 24 is configured to convert the outputs of the charge/voltage converter 23 into digital signals. The parallel/serial converter 25 is configured to convert the image signals, which are read out in parallel on a line basis from the flat detector 21, into serial signals.

The high-voltage generation unit 3 is configured to generate a high voltage to be applied between the anode and the cathode of the X-ray tube 1*a* for accelerating the thermal electrons generated from the cathode. The holding arm 4 is configured to join and hold the X-ray generation unit 1 and the X-ray detection unit 2.

The mechanism unit 5 is configured to drive the mechanisms of some units of the X-ray diagnostic apparatus 100, and includes a holding-arm movement mechanism 51, a bed movement mechanism 52, and a grid attachment/detachment mechanism 53. The holding-arm movement mechanism 51 is configured to move the X-ray generation unit 1 and the X-ray detection unit 2 relative to the direction of the body axis of the subject P to determine the cross section to be imaged. The bed movement mechanism 52 is configured to move the bed (top plate) B horizontally or vertically. The grid attachment/detachment mechanism 53 is configured to attach and detach the grid 20 which is designed to be disposed between the flat detector 21 and the bed (top plate) B for the removable of scattered X rays.

The mechanism control unit 6 is configured to control the drive of the mechanism unit 5, which is formed of the holding-arm movement mechanism 51, the bed movement mechanism 52, and the grid attachment/detachment mechanism 53, on the basis of control signals from the system control unit 10 described later.

The image creation unit 7 is formed of an image computation unit 71, a display image memory 72, and an image processing unit 73. The image computation unit 71 is configured to receive the X-ray transmission information obtained by the X-ray detection unit 2 and perform image processing computation aimed at edge enhancement, improvement in S/N ratio, and the like on the basis of the X-ray transmission information. The display image memory 72 is configured to temporarily store the X-ray image data having been subjected to the image processing computation in the image computation unit 71. The image processing unit 73 is configured to perform processing for conversion into an X-ray image for display on the basis of the X-ray image data thus created.

The notification unit 8 is a display device configured to display the X-ray image subjected to the sensitivity correction in the image creation unit 7. As the notification unit 8, a CRT monitor, an LCD monitor, and the like are available, for example.

The operation unit 9 is an interactive interface including a keyboard, various switches, a mouse, and the like. The operator of the X-ray diagnostic apparatus 100 uses the operation unit 9 to input command signals about various imaging conditions such as the tube voltage and the tube current to be applied to the X-ray tube 2a, the duration of X-ray irradiation, and the like, as well as the start of the examination, the control of the movements of the mechanism unit 5, and the like, for example. These command signals are sent to the corresponding units through the system control unit 10.

The system control unit 10 includes at least a CPU and a storage circuit which are unillustrated. The system control unit 10 is configured to temporarily store the information sent through the operation unit 9, such as the operator's instructions and the imaging conditions, and then perform control on the whole system forming the X-ray diagnostic apparatus 100 on the basis of the information, the control including controlling the collection and display of the X-ray transmission information, controlling the movement mechanisms, and the like.

The storage unit 12 is formed of a semiconductor or magnetic disk, for example, and is configured to store various types of information in the X-ray diagnostic apparatus 100.

Figure 2:
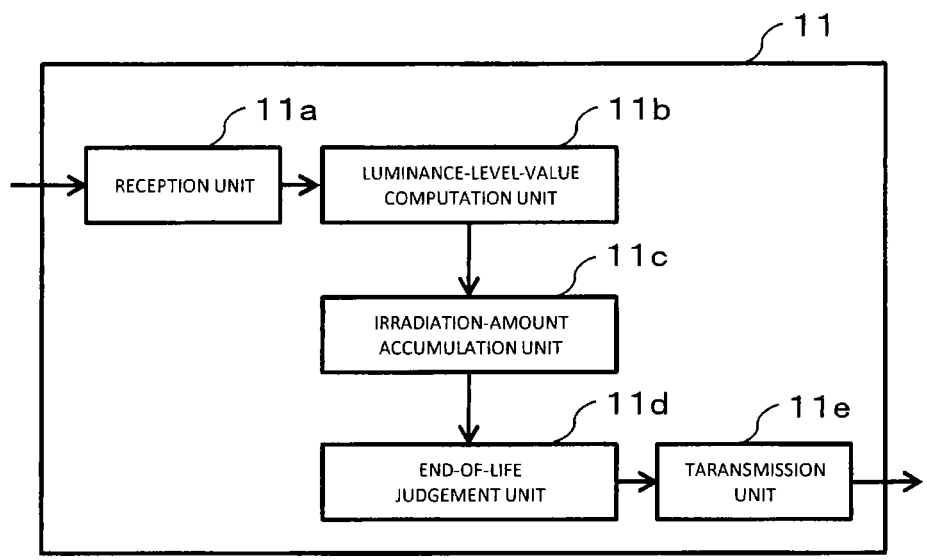
FIG. 2 is a block diagram showing the inner configuration of an end-of-life detection unit in the first embodiment.

FIG. 2 is a block diagram showing the inner configuration of the end-of-life detection unit 11 in the first embodiment. The end-of-life detection unit 11 has a function of detecting the end of life of the flat detector 21 on the basis of the amount of X-ray irradiation. To do so, the end-of-life detection unit 11 includes a reception unit 11a, a luminance-level-value computation unit 11b, an irradiation-amount accumulation unit 11c, an end-of-life judgment unit 11d, and a transmission unit 11e. The function of each unit of the end-of-life detection unit 11 will be described together with the description of procedures for detecting the end of life of the flat detector.

Figure 3:
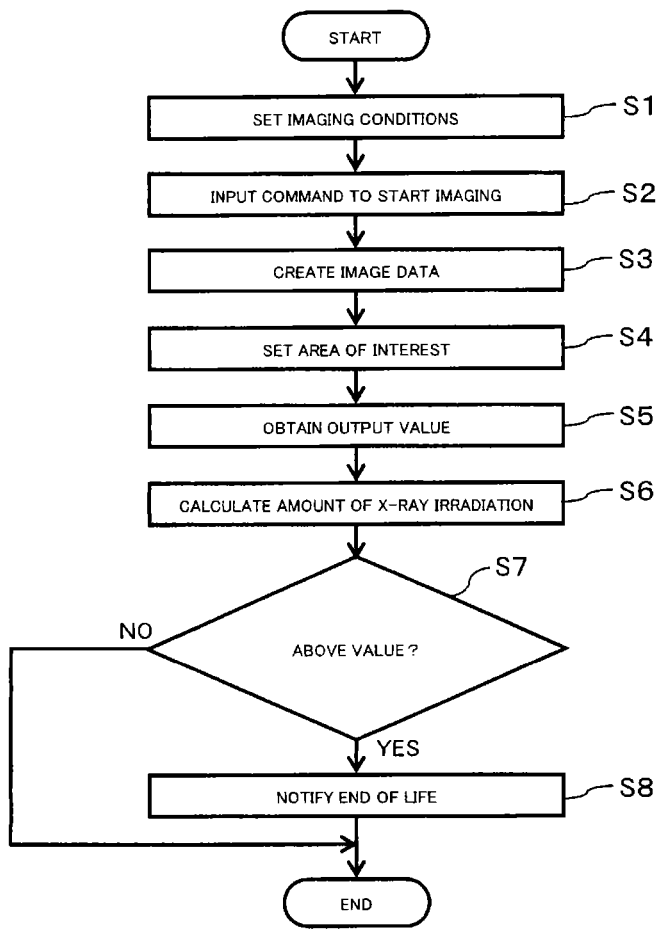
FIG. 3 is a flowchart showing the procedures for detecting the end of life of a flat detector of an X-ray detection unit in the first embodiment.

FIG. 3 is a flowchart showing the procedures for detecting the end of life of the flat detector 21 of the X-ray detection unit in the first embodiment. Here, "the end of life" in "the procedures for detecting the end of life" to be described below refers to the deterioration of the sensitivity of the flat detector 21.

As mentioned above, the flat detector 21 receives irradiation of X rays while X-ray imaging is performed. Internal information of the subject P is obtained by causing the image creation unit 7 to create an image on the basis of X rays detected by the flat detector 21, and causing the notification unit 8 to display it. Thus, deterioration in the sensitivity of the flat detector 21 makes it impossible to obtain necessary information if the image is finally displayed on the notification unit 8 as a medical image.

In this respect, in this embodiment, the amount of X-ray irradiation of the flat detector 21 is calculated, and this amount of X-ray irradiation and the previous amount (s) of X-ray irradiation of the flat detector 21 are used to calculate the total accumulated amount of X-ray irradiation of the flat detector 21. Then, based on the accumulated amount of irradiation thus calculated, it is checked whether the flat detector 21 has received irradiation of X rays above a predetermined amount, and if so, the flat detector 21 is judged as having reached the end of its life. It is also possible to judge whether or not the flat detector 21 is near the end of its life, before it is judged as having reached the end of life. Then, if the flat detector 21 has reached or is near the end of its life, such information is notified to the operator or the like.

In the following, description will be given of operations related to the calculation of the accumulated amount of X-ray irradiation of the flat detector 21, as well as the judgment on the end of its life and the notification thereof.

Specifically, the operator of the X-ray diagnostic apparatus 100 uses the operation unit 9 to input and set up various imaging conditions for normal imaging, for example (S1). More specifically, based on inputs from the operation unit 9, instruction signals are supplied to the holding-arm movement mechanism 51 and the bed movement mechanism 52 through the system control unit 10 and the mechanism control unit 6. Then, the imaging part of the subject P is set to be positioned properly with respect to the X-ray generation unit 1 and the X-ray detection unit 2. Moreover, various parameters necessary for the imaging are set in the X-ray generation unit 1 as well. These imaging conditions thus set are stored in the unillustrated storage circuit of the system control unit 10.

Then, the X-ray diagnostic apparatus 100 receives a command to start the normal imaging for an X-ray transmission image inputted by the operator through the operation unit 9 (S2). When the system control unit 10 is supplied with this imaging start command through the operation unit 9, the system control unit 10 sends a drive signal to the high-voltage generation unit 3 on the basis of the set conditions. An output voltage of the high-voltage generation unit 3 generated based on this drive signal is applied to the X-ray tube 1a of the X-ray generation unit 1. The X-ray tube 1a in turn irradiates to the subject P with X rays. The X rays having been transmitted through the subject P travel through the grid 20 disposed downstream of the subject P and are detected by the flat detector 21.

The flat detector 21 is formed of multiple detection elements arranged two-dimensionally in an array of M detection elements in the line direction and N detection elements in the column direction, for example. In this flat detector 21, the drive terminals of the M detection elements arranged in the line direction are commonly connected and are connected to the output terminal of the gate driver 22. On the other hand, the output terminals of the N detection elements arranged in the column direction are commonly connected through a signal output line (unillustrated), and this signal output line is connected to the input terminal of the charge/voltage converter 23.

In order for the charges stored in the detection elements to be read out to the signal output line through the TFTs (unillustrated), the gate driver 22 supplies the gate terminals of the TFTs with a drive pulse for readout (ON voltage) through a drive circuit. By supplying this drive pulse to the gate terminals, the TFTs are brought into a conductive (ON) state, so that signal charges stored in charge storage capacitors (unillustrated) are outputted to the signal output line. The signal charges are converted from charges into voltages by the charge/voltage converter 23 and further converted into digital signals by the A/D converter 24.

The system control unit 10 inputs the outputs of the A/D converter 24 in parallel into a memory of the parallel/serial converter 25 and temporarily store them therein. Then, the system control unit 10 reads out the outputs in serial and transmits the X-ray transmission information to the image creation unit 7. Upon receipt of the X-ray transmission information, the image creation unit 7 creates an X-ray image to be displayed on the notification unit 8 (S3).

Next, the setting of an area of interest (S4) will be described. As mentioned above, the end of life (sensitivity deterioration) of the flat detector 21 is detected based on the amount of X-ray irradiation of the flat detector 21. To calculate the total accumulated amount of irradiation in which the amount of X rays in each irradiation is accumulated, an area through which to detect the amount of X-ray irradiation is necessary in the flat detector 21. Thus, at least one area of interest being the area through which to detect the amount of X-ray irradiation is set within the X-ray irradiation surface of the flat detector 21, and the accumulated amount of irradiation is calculated for each area of interest.

Here, a target on which to set the area of interest is mentioned as "the X-ray irradiation surface of the flat detector 21". However, the amount of X-ray irradiation is detected based on the X-ray image created by the image processing unit 73, and therefore the target on which to set the area of interest is this "X-ray image." Note that while the area of interest can be set on the X-ray image as described above, the area of interest may instead be set on the detector 21 by hardware. Accordingly, in the following description, an expression such as "the area of interest is set on the flat detector 21" will be described when appropriate.

Here, a case where one area of interest is set includes a case where the area of interest is set by taking the whole area of the flat detector 21 as one area.

Figure 4:
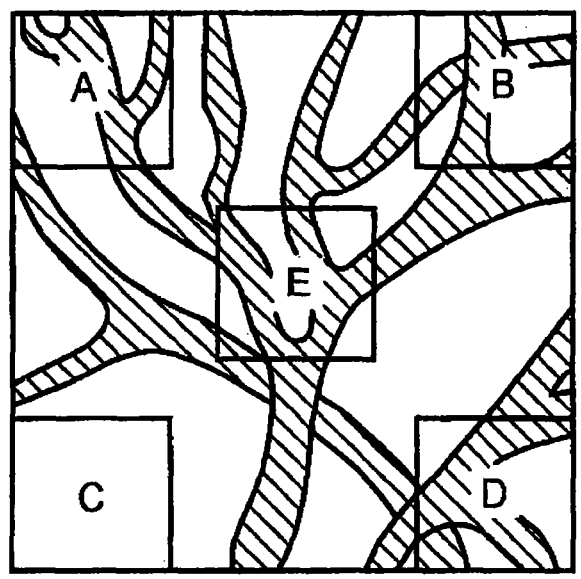
FIG. 4 is a diagram showing some examples of an area of interest set according to the first embodiment.

On the other hand, in a case where multiple areas of interest are set on the flat detector 21, it is possible to set the areas of interest in a way as shown in FIG. 4, for example. FIG. 4 is a diagram showing an example of the areas of interest set according to the first embodiment. In the flat detector 21 shown in FIG. 4, a total of five areas of interest (areas A to E) are set at the four corners and the center of the flat detector 21, respectively.

Meanwhile, when the area to be irradiated with X rays is narrowed by the X-ray diaphragm 1b, the X rays are transmitted through the subject P in a narrowed state. As an X-ray image is created based on the resultant X-ray transmission information, a peripheral area where the subject P is not captured appears around the X-ray image. In this case, it is possible, for example, to set five separate areas of interest as mentioned above within the narrowed X-ray irradiation area (the area to create an X-ray image), and in addition, to provide an area of interest on the flat detector 21 in an area outside the X-ray irradiation area (the peripheral area where the subject P is not captured).

Further, multiple areas of interest may be set such that they are completely independent areas with no overlaps or that they differ from each other at least partially.

As described above, the position, size, and shape of the area of interest set on the flat detector 21, as well as the number thereof and the like can be set as desired. The area of interest thus set is stored in the storage unit 12, for example.

Meanwhile, the configuration may be set such that the area of interest is changed depending on the body part of the subject P to be imaged by the X-ray diagnostic apparatus 100 or the like. Alternatively, the configuration may be set such that the set area of interest is not changed under any circumstance, irrespective of the body part or the like.

Moreover, in the first embodiment, while the area of interest can be set in this step (step S4) as mentioned above, the area of interest may be set in advance, before the creation of X-ray image data described in step S3, for example. Alternatively, the area of interest may be set before the examination (imaging of the subject P) is performed in the X-ray diagnostic apparatus 100 in the first place, e.g. when the X-ray diagnostic apparatus 100 is installed or activated.

As mentioned above, the X-ray image created by the image processing unit 73 of the image creation unit 7 is sent to the end-of-life detection unit 11, in which the reception unit 11a obtains the X-ray image. Thereafter, the X-ray image is sent to the luminance-level-value computation unit 11b. Based on the acquired X-ray image, the luminance-level-value computation tool 11b reads out information on the area of interest set in advance on the flat detector 21 (X-ray image) from the storage unit 12. Then, the luminance-level-value computation unit 11b obtains the output value of the X-ray image data corresponding to the area of interest (S5 in FIG. 3). Here, the output value of the irradiation in the area of interest is obtained for each area of interest.

Specifically, the luminance-level-value computation unit 11b obtains the output value (the amount of irradiation) of the X-ray image as follows. Here, an example of the method of calculating the output value of the X-ray image will be described by using FIG. 4 again. FIG. 4 is a diagram showing an example of the area of interest set in the first embodiment and showing the method of the output value calculation by the luminance-level-value computation unit 11b.

The operator sets in advance areas of interest (areas A, B, C, D, and E at mutually different positions shown in FIG. 4) on the X-ray image. The luminance-level-value computation unit 11b then adds up the luminance values within each area to calculate the output value of each area (area of interest).

Figure 5:
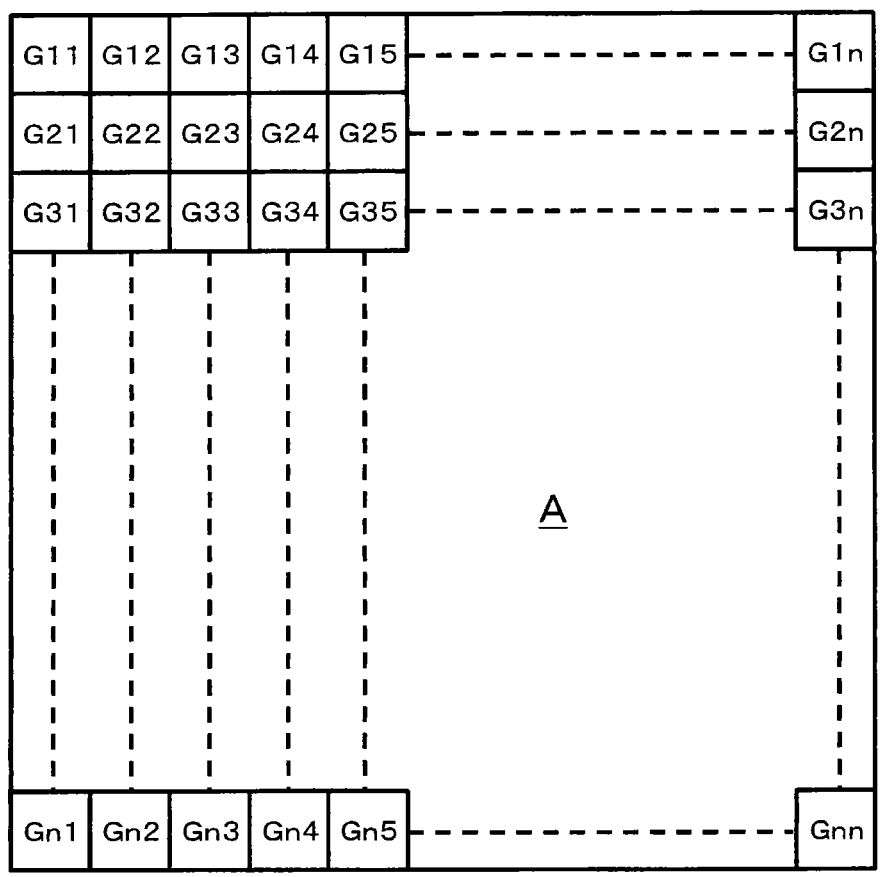
FIG. 5 is a diagram showing a method of calculation of an output value by a luminance-level-value computation unit in the first embodiment.

FIG. 5 is a diagram showing the method of the calculation of the output value by the luminance-level-value computation unit 11b in the first embodiment. In a case where the luminance value of each pixel of the X-ray image data forming the area A shown in FIG. 4 is as shown in FIG. 5, for example, an output value GL(A) of the area A (the luminance level value within the area of interest) can be found from the following expression.

$$GL(A)=(G11+G12+\ldots+G1n)+(G21+G22+\ldots+G2n)+\ldots+(Gn1+Gn2+\ldots+Gnn)$$

Since the luminance-level-value computation unit 11b obtains the output value for each area of interest as mentioned above, the luminance-level-value computation unit 11b calculates the output values of the areas other than the area A by using the same method.

Note that besides the simple addition described above, a method of calculating a mean value or a method using weighted addition may be employed.

Thereafter, the irradiation-amount accumulation unit 11c selects a corresponding relational expression from among multiple relational expressions each of which is stored in the storage unit 12 and represents the relation between the output value of the X-ray image data and the amount of X-ray irradiation. Then, the irradiation-amount accumulation unit 11c puts the calculated output value of the X-ray image data into the relational expression to calculate the amount of X-ray irradiation of each area of the interest. Here, the corresponding relational expression is a relational expression shown by the solid line in the graph of FIG. 6, for example.

Figure 6:
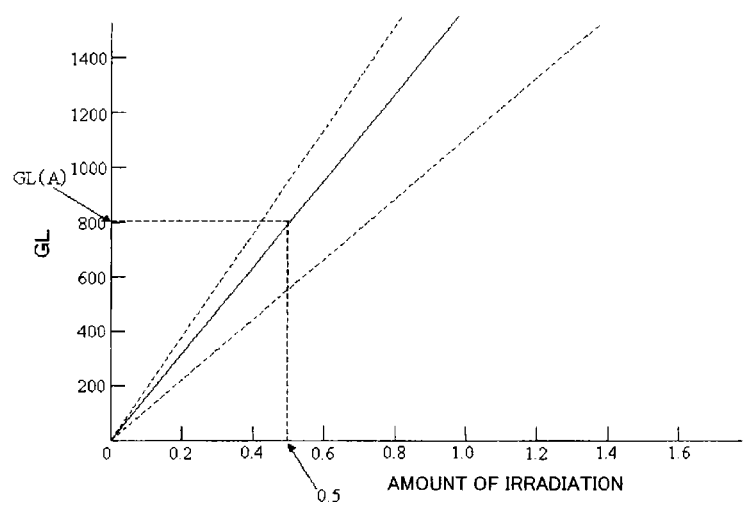
FIG. 6 is a graph showing a method of calculation of the amount of X-ray irradiation from the output value in the first embodiment.

The storage unit 12 stores the relational expression between the output value and the amount of X-ray irradiation as shown in FIG. 6 for each combination of X-ray irradiation conditions (tube voltage, tube current, pulse width, etc.). The irradiation-amount accumulation unit 11c selects the relational expression that corresponds to the combination of the set X-ray irradiation conditions, and calculates the amount of X-ray irradiation on the basis of the relational expression and the output value sent from the luminance-level-value computation unit 11b.

Suppose that the output value GL(A) of the area A of the aforementioned areas of interest shown in FIG. 4 is 800, for example. In this case, the amount of irradiation thereof can be calculated to be 0.5 by using the relational expression shown in FIG. 6.

Note that each relational expression between the output value and the amount of X-ray irradiation as shown in FIG. 6 may be stored in the storage unit 12 or stored in the irradiation-amount accumulation unit 11c. Moreover, in respect to the relational expression between the output value and the amount of X-ray irradiation, a relational expression (graph) can be created while taking into consideration various imaging conditions such as the amount of irradiation of X rays (kV) from the X-ray generation unit 1, for example.

Moreover, the irradiation-amount accumulation unit 11c calculates the accumulated amount of irradiation for each area of interest by adding the amount of X-ray irradiation calculated this time to the total value of the amounts of X-ray irradiation (the value of the accumulated amount of irradiation amount) stored in the storage unit 12 or in the irradiation-amount accumulation unit 11c itself (S6). The total value includes the amount of the first and, if any, subsequent X-ray irradiation in the area of interest. Each accumulated amount of irradiation thus calculated is sent to the end-of-life judgment unit 11d.

Note that each accumulated amount of irradiation is obtained by adding up the amounts of the previous X-ray irradiation, regardless of whether the power of the apparatus is on or off. Upon replacement of the detector or the like, each accumulated amount of irradiation can be reset by performing a predetermined reset input. Moreover, each accumulated amount of irradiation is preferably stored in a non-volatile memory or the like so that the data will not be erased unless a reset input is performed.

Moreover, the end-of-life judgment unit 11d compares each latest accumulated amount of X-ray irradiation updated by adding up the amounts of previous X-ray irradiation, with a threshold for the amount of X-ray irradiation which is stored in advance in the storage unit 12 and indicates the end of life of the flat detector 21 (S7). If the accumulated amount of X-ray irradiation is above the threshold, the end-of-life judgment unit 11d judges that the flat detector 21 has reached the end of its life. Meanwhile, multiple thresholds may be set. In this way, it is possible to judge when the end of life is about to come on a step-by-step basis. This allows one to judge whether the flat detector 21 is near the end of its life, for example.

If the comparison result shows that the accumulated amount of X-ray irradiation is above the threshold in one of the areas of interest (YES in S7), an instruction signal is sent to the notification unit 8 to instruct it to output a display notifying the operator of such information. In response to the signal, the notification unit 8 outputs the display notifying that the flat detector 21 has reached the end of its life (S8). On the other hand, if the accumulated amount of X-ray irradiation is below the threshold (NO in S7), no instruction signal is transmitted to the notification unit 8.

As for the method of displaying that the information that the flat detector 21 has reached the end of its life, various methods are possible as shown in FIGS. 7 to 10 below. FIGS. 7 to 10 are diagrams showing examples of the display on the notification unit in the first embodiment.

Figure 7:
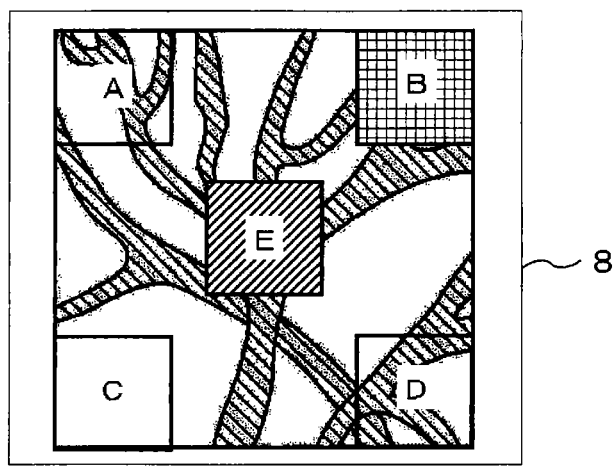
FIG. 7 is a diagram showing an example of a display on a notification unit in the first embodiment.
Figure 8:
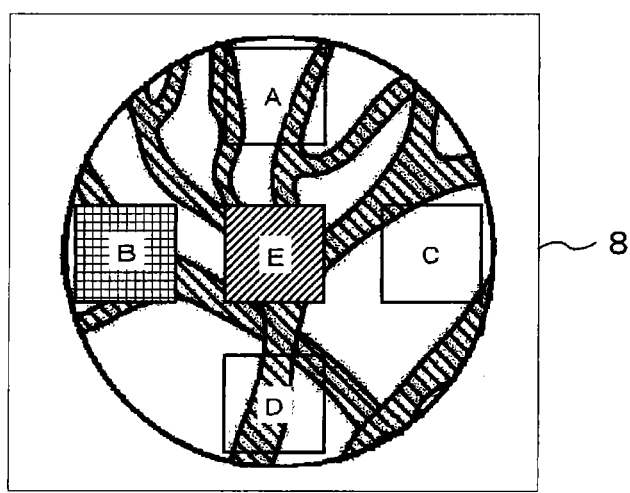
FIG. 8 is a diagram showing an example of the display on the notification unit in the first embodiment.

FIG. 7 is a display example of the notification unit 8 in a case where the flat detector 21 is an FPD. Moreover, FIG. 8 is a display example in a case where the flat detector 21 is an I.I. In the case of the screen example shown in FIG. 7, of five areas of interest A to E set on X-ray image data, the areas with the largest and smallest accumulated amounts of X-ray irradiation are illustrated in colors different from the other areas (for convenience, in the drawing, these areas are shown by diagonal lines and a lattice instead of colors).

FIG. 7 shows that the area E (at a center portion of the flat detector 21) has the largest accumulated amount of X-ray irradiation while the area B (at the upper right corner of the flat detector 21) has the smallest accumulated amount of X-ray irradiation, for example. Meanwhile, when the flat detector 21 is an I.I., the field of view is circular unlike FPDs, and therefore the display example shown in FIG. 8 is illustrated in a circular shape as well. In this case, areas of interest are provided respectively at five positions that divide the field of view in a cross shape. In this example too, a center portion of the flat detector (area E) has the largest accumulated amount of irradiation. On the other hand, an area B is set on the middle left, and this area has the smallest accumulated amount of irradiation.

Figure 9:
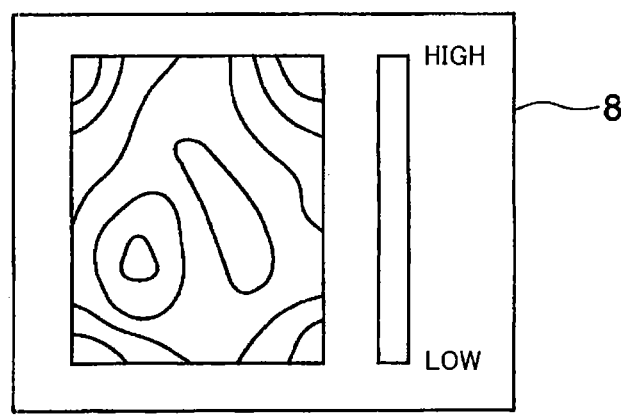
FIG. 9 is a diagram showing an example of the display on the notification unit in the first embodiment.

In FIG. 9, the accumulated amount of X-ray irradiation in the whole area of the flat detector 21 is shown by, for example, calculating the accumulated amount of X-ray irradiation for each cell and by connecting spots having accumulated amounts of irradiation indicating the same or similar values, i.e., like contour lines. Moreover, the spots having accumulated amounts of irradiation indicating the same or similar values are illustrated in colors which respectively correspond to the accumulated amounts of irradiation. In this way, the X-ray image data can be displayed in a fashion more understandable for the operator. In FIG. 9, a bar shown beside the displayed accumulated amounts of X-ray irradiation shows the level of the accumulated amount of irradiation, and the color displayed therein shifts from the highest to the lowest level, for example.

Figure 10:
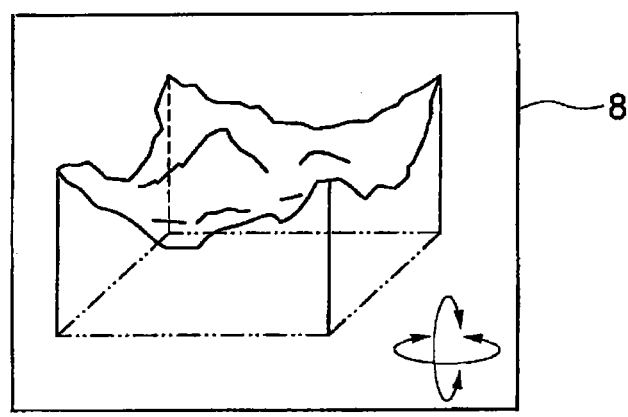
FIG. 10 is a diagram showing an example of the display on the notification unit in the first embodiment.

Meanwhile, in FIG. 10, instead of showing the accumulated amount of irradiation for each area of interest, the accumulated amount of X-ray irradiation is shown for each cell in height, for example. In this case, areas located at visually high positions indicate that their accumulated amounts of irradiation are accordingly larger than the other areas. In the display shown in FIG. 10, the portion indicated by the two-dot chain line is assumed as the front surface of the flat detector 21 (the surface which actually receives irradiation of X rays). With this surface as a reference, distance (height) in the height direction shows the level of X-ray irradiation. Moreover, due to the use of the length and width of the surface, as well as the use of height to show the accumulated amount of irradiation at each spot, the display image is shown three dimensionally.

In the display example shown in FIG. 10, the accumulated amount of X-ray irradiation is large at the four corners of the flat detector 21. A center portion has a spot with a large accumulated amount of irradiation, but this accumulated amount of irradiation is considered small as compared to those of the four corners. From this display, it is possible to intuitively know that the imaging part of the subject P is situated on the center portion of the flat detector 21 and therefore the flat detector 21 is not irradiated directly with X rays, for example. Moreover, this display can be rotated and so on as needed so that the operator can easily see it.

Meanwhile, although not shown in FIG. 10, a plane representing the end of life may be shown at an opposed position above the front surface of the flat detector 21 (the plane indicated by the two-dot chain line) in the height direction, for example. By setting this plane, it is possible to visually recognize that an area has reached the end of life when the accumulated amount of irradiation of this area reaches the plane.

As described above, the X-ray image data is displayed in such a fashion that the operator can visually recognize which area has a large accumulated amount of X-ray irradiation and which area has a small accumulated amount of X-ray irradiation. Such display allows the presentation of the condition of use in each imaging to the operator. Accordingly, in a case of FIG. 7 for example, the operator can perform imaging in such a way that a lesion part and its peripheral part requiring careful reading are not included in the area E which has the largest accumulated amount of X-ray irradiation and is therefore lower than other areas in the reliability of X-ray image data obtained therefrom. Moreover, the whole flat detector can be used evenly, thereby resulting in extension of the life of the flat detector.

The description is given here by taking various display examples which visually notify the operator that the flat detector 21 is near the end of its life. Note, however, that the operator may be notified by using some other method that stimulates the operator's senses such as a method which notifies the operator by making a sound with an unillustrated microphone or the like.

Alternatively, the condition of use of the flat detector can be notified, instead of notifying the end of life. In this case, the display unit 8 is caused notify the state of the flat detector as the condition of use even when the accumulated amount of X-ray irradiation is below the threshold (NO in S7). The condition of use can be notified by outputting a specific number such for example as 50% in accordance with the end of life, for example. Alternatively, the current condition of the flat detector may be shown on a number line showing the start of use to the end of life. Moreover, not only is the condition of use notified, but the time of the end of life may be estimated based on the judgment result and notified.

According to the embodiment described above, an X-ray diagnostic apparatus can be provided which is capable of more accurately figuring out and notifying the end of life of a detector included in the X-ray diagnostic apparatus. In addition, besides the total accumulated amount of X-ray irradiation of the detector including the previous X-ray irradiation, as a matter of course, the amount of irradiation of the detector can be estimated on an examination basis or on a day basis, thereby improving the serviceability of the apparatus.

Meanwhile, a single X-ray diagnostic apparatus 100 has heretofore been taken as an example and the description has been given of the detection and notification of the end of life of the flat detector 21 used in this X-ray diagnostic apparatus 100. Thus, the notification here is addressed to the operator of the X-ray diagnostic apparatus 100.

On the other hand, in a case where there are multiple X-ray diagnostic apparatuses 100A to 100C, for example, the configuration may be set such that the end of life of each of the X-ray diagnostic apparatuses 100A to 100C is detected and notified to a person maintaining these X-ray diagnostic apparatuses.

Figure 11:
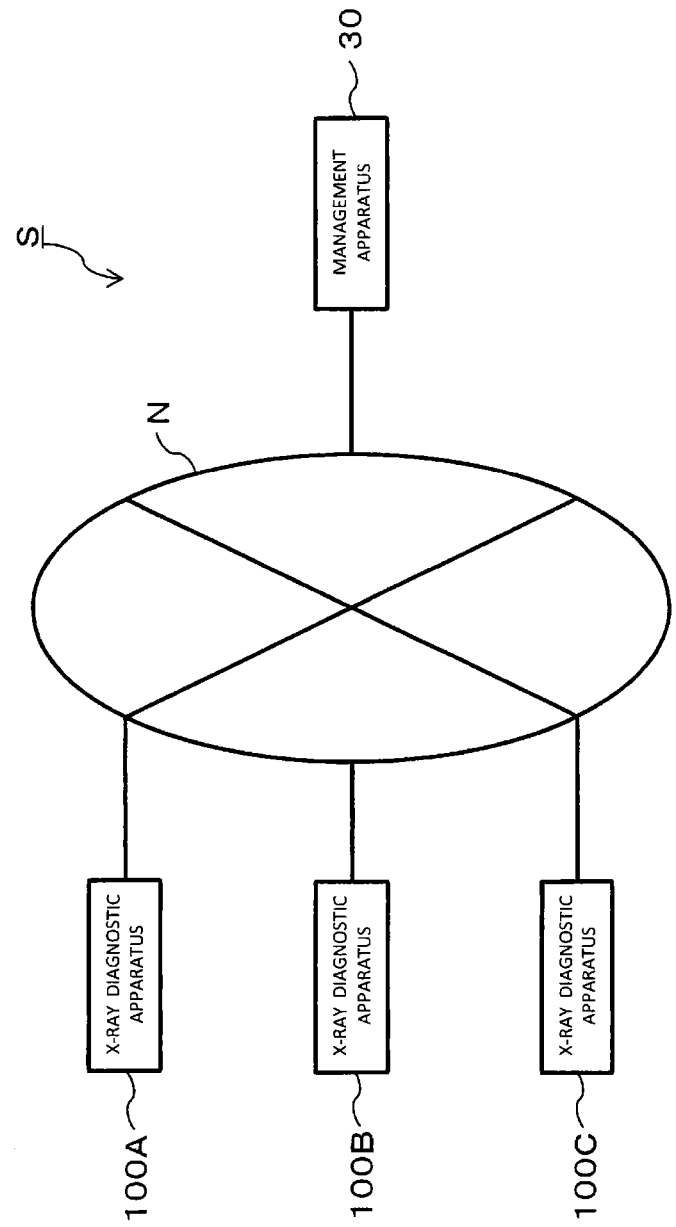
FIG. 11 is a block diagram showing another notification method in the first embodiment.

FIG. 11 is a block diagram showing another notification method in the first embodiment. In a management system S shown in FIG. 11, the multiple X-ray diagnostic apparatuses 100A to 100C and a management apparatus 30 are connected to a communication network N. Here, the management apparatus 30 remotely monitors the X-ray diagnostic apparatuses 100A to 100C and, if any of their flat detectors has reached the end of life, the management apparatus receives a notification of such information from the corresponding X-ray diagnostic apparatus, for example.

Note that the management apparatus 30 may be provided inside the medical facility in which the X-ray diagnostic apparatuses 100A to 100C are installed, or provided outside this medical facility.

By employing such a configuration, the aforementioned advantageous effects can be provided as a matter of course, and further, the maintenance personnel operating the management apparatus can perform the replacement of the flat detector (s) and the like at appropriate timings on the basis of the notification. Accordingly, actions can be taken against the end of life of the flat detector more quickly than before. Moreover, by notifying a time (period) left until the end of life, for example, a proper and sufficient service can be provided for the end of life that will come later in time.

(Second Embodiment)

Next, a second embodiment of the present invention will be described. Note that in the second embodiment, the same components as the components described in the foregoing first embodiment are denoted by the same respective reference numerals, and overlapping descriptions of these same components are omitted.

An X-ray diagnostic apparatus 200 in the second embodiment is characterized in that the X-ray generation unit 1 and the X-ray detection unit 2 in the first embodiment are separated from each other. In other words, the flat detector and the mechanism to detect the end of life of the flat detector are designed to be portable, for example.

Figure 12:
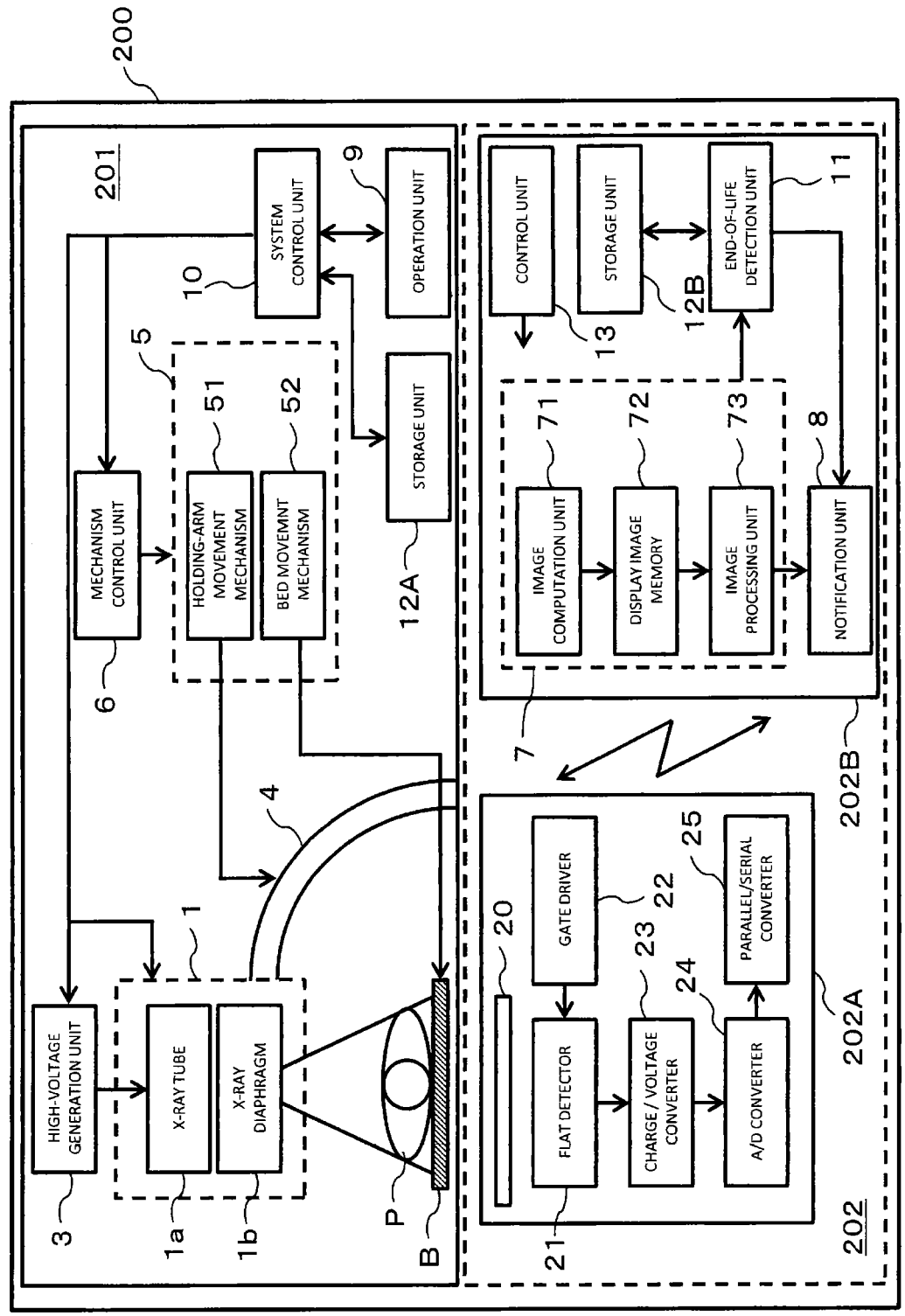
FIG. 12 is an overall diagram showing a schematic configuration of an X-ray diagnostic apparatus in a second embodiment.

As shown in FIG. 12, the X-ray diagnostic apparatus 200 in the second embodiment is formed of an X-ray generation device 201 and an image collection device 202. Note that the second embodiment is described on the assumption that the X-ray generation device 201 and the image collection device 202 are separated from each other; however, while a detector main unit 202A in the image collection device 202 is separated from the X-ray generation device 201, a detector control unit 202B in the image collection device 202 may be configured integrally with the X-ray generation device 201.

The X-ray generation device 201 includes an X-ray generation unit 1 configured to generate X rays with which a subject P is to be irradiated, a high-voltage generation unit 3, a mechanism control unit 6 configured to control the drive of various mechanisms such as a holding arm 4 and a bed (top plate) B, and the like. The X-ray generation device 201 also includes an operation unit 9 which the operator uses to operate the mechanisms, a system control unit 10 configured to control the whole X-ray generation device 201, and a storage unit 12A.

Note that for the X-ray generation device 201 in the second embodiment, only the functions that are considered necessary in the description of the second embodiment are shown. Thus, mechanisms which are not illustrated in FIG. 12 but are supposed to be included in the X-ray generation device 201 are included in the X-ray generation device 201, as a matter of course.

On the other hand, the image collection device 202 in the second embodiment is a wireless type and is formed of the detector main unit 202A connected to the X-ray generation device 201 and the detector control unit 202B configured to transmit a control signal to the detector main unit 202A and to do the like.

First, like the X-ray detector unit 2 in the foregoing first embodiment, the detector main unit 202A includes a grid 20, a flat detector 21, a gate driver 22, a charge/voltage converter 23, an A/D converter 24, and a parallel/serial converter 25. The functions of these components are as described earlier.

Note that since the image collection device 202 is a wireless type, the gate driver 22 drives the detection elements of the detector 21 on the basis of an instruction from the detector control unit 202B, for example. Besides this controlling of the drive of the detector 21, the transmission of converted electric signals to an image creation unit 7 is performed in this manner through radio (wireless) transmission, instead of using cable (wired) transmission.

The detector control unit 202B is formed of the image creation unit 7, a notification unit 8, an end-of-life detection unit 11, a control unit 13, and a storage unit 12B. In this embodiment of the present invention, the detector control unit 202B wirelessly transmits a control instruction to the detector main unit 202A to control the whole image collection device 202. The configurations and functions of the image creation unit 7, the notification unit 8, and the end-of-life detection unit 11 are as described in the first embodiment.

The control unit 13 is configured to control the drive of the whole image collection device 202. Note that in FIG. 12, the control unit 13 is not directly connected to each unit of the detector control unit 202B and there is only an arrow extending therefrom. This is because the control unit 13 is shown by omitting its connection to each unit.

The storage unit 12B is configured to store internal information on the subject P obtained by the X-ray diagnostic apparatus 200. The target to be stored in the storage unit 12B may be the very internal information on the subject P transmitted from the detector main unit 202A, a medical image created by the image creation unit 7, or the previous amounts of X-ray irradiation used to judge the end of life of the flat detector 21. Note that the storage unit 12B may be connected to some other medical diagnostic imaging apparatus or the like through an unillustrated communication network.

The configuration of the X-ray diagnostic apparatus 200 in the second embodiment is as described above. As mentioned above, the detector main unit 202A of the image collection device 202 receives X ray irradiation from the X-ray generation device 201, converts the X rays into signals and then transmits them to the detector control unit 202B. The image creation unit 7 of the detector control unit 202B creates X-ray image data, and then the end-of-life detection unit 11 checks the end of life of the flat detector 21 by using the this data. The result of a judgment made by the end-of-life judgment unit 11d is notified to the operator through the notification unit 8.

According to the second embodiment described above, an X-ray diagnostic apparatus can be provided which is capable of more accurately figuring out and notifying the end of life of a detector of an image collection device. In addition, besides the total accumulated amount of X-ray irradiation of the detector including the previous X-ray irradiation, as a matter of course, the amount of irradiation of the detector can be estimated on an examination basis and on a day basis, thereby improving the serviceability of the apparatus.

In particular, since the image collection device including the flat detector is in a portable form, it is possible to use the image collection device in various ways in combination with various X-ray generation devices. Thus, in light of the function of the image collection device, figuring out how much life is left in the flat detector is essential as compared to a case of a stationary X-ray diagnostic apparatus. As described in the second embodiment, the image collection device has a function of detecting the end of life of the flat detector, and actions can therefore be taken against the end of life of the flat detector more quickly and flexibly.

(Third Embodiment)

Next, a third embodiment of the present invention will be described. Note that in the third embodiment, the same components as the components described in the foregoing first or second embodiment are denoted by the same respective reference numerals, and overlapping descriptions of these same components are omitted.

In the above description of both the first and second embodiments, to detect the end of life of the flat detector, the end-of-life detection unit finds output values from an X-ray image, converts the output values into the amounts of X-ray irradiation, and then finds the accumulated amount of irradiation for each area of interest. The end-of-life detection unit then uses this accumulated amount of irradiation to judge whether or not the flat detector has reached the end of life.

On the other hand, as will be described in this third embodiment, besides this method of judging the end of life of the flat detector, it is possible to employ a method in which the end of life of the flat detector is judged based on the pixel value of the flat detector (in each area of interest), for example.

Figure 13:
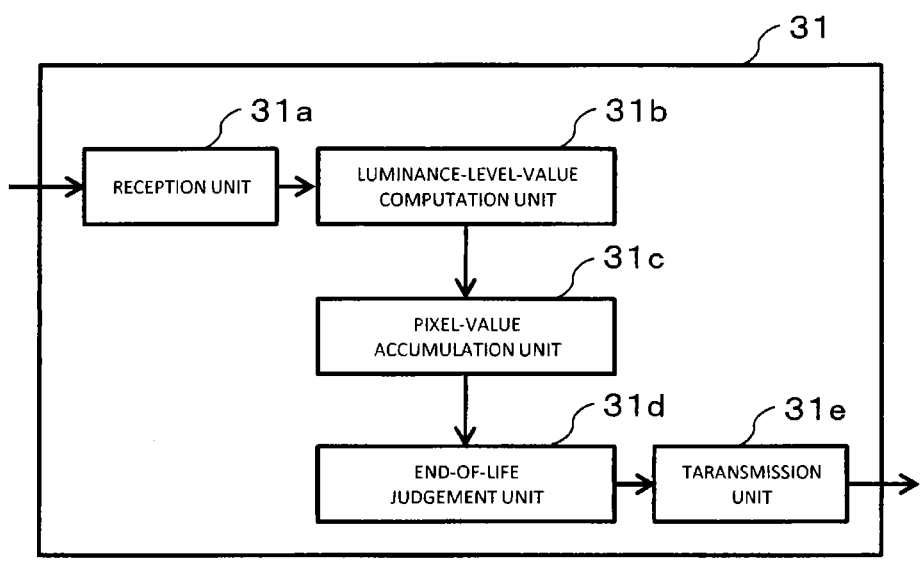
FIG. 13 is a block diagram showing the inner configuration of an end-of-life detection unit in a third embodiment.

FIG. 13 is a block diagram showing the inner configuration of an end-of-life detection unit 31 in the third embodiment. The end-of-life detection unit 31 includes a reception unit 31a, a luminous-level-value computation unit 31b, a pixel-value accumulation unit 31c, an end-of-life judgment unit 31d, and a transmission unit 31e.

After acquiring an X-ray image from an image processing unit 73, the end-of-life detection unit 31 (reception unit 31a) transmits that information to the luminous-level-value computation unit 31b. The luminous-level-value computation unit 31b calculates, for each area of interest set in the X-ray image, the pixel value of the area of interest. Each calculated pixel value is sent to the pixel-value accumulation unit 31c. The pixel-value accumulation unit 31c adds each calculated pixel value to the previous pixel value of the corresponding area of interest to calculate the accumulated pixel value of each area of interest. Each accumulated pixel value is further sent to the end-of-life judgment unit 31d, where the end of life of the detector is judged based on the accumulated pixel value.

By judging the end of life of the detector as described above, it is possible to omit part of the computation process as compared to the case where the judgment is made from the output value.

Note that employing the above judgment method provides the following advantageous effects, as a matter of course. Specifically, an X-ray diagnostic apparatus can be provided which is capable of more accurately figuring out and notifying the end of life of a detector forming the X-ray diagnostic apparatus. In addition, besides the total accumulated amount of X-ray irradiation of the detector including the previous X-ray irradiation, as a matter of course, the amount of irradiation of the detector can be estimated on an examination basis and on a day basis, thereby improving the serviceability of the apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray generation unit configured to generate an X ray with which a subject is to be irradiated;
an X-ray detection unit including a detector and configured to create X-ray transmission information, the detector being configured to detect the X ray transmitted through the subject;
an image creation unit configured to create an X-ray image on the basis of the X-ray transmission information; and
an end-of-life detection unit configured to detect an end of life of the detector on the basis of an output value in the X-ray image, wherein
the end-of-life detection unit includes
a luminance-level-value computation unit configured to calculate an amount of X-ray irradiation of the detector on the basis of the output value in an area of interest which is set on any one of the X-ray image and the detector,
an irradiation-amount accumulation unit configured to calculate an accumulated amount of irradiation in the area of interest by adding the amount of X-ray irradiation calculated by the luminance-level-value computation unit to a previous amount of X-ray irradiation in the area of interest, and
an end-of-life judgment unit configured to make a judgment on the end of life of the detector on the basis of the accumulated amount of irradiation.

2. The X-ray diagnostic apparatus according to claim 1, wherein the area of interest is set as any one of a single area and a plurality of areas on the X-ray image.

3. The X-ray diagnostic apparatus according to claim 1, wherein in a case where the X-ray is transmitted through the subject in a narrowed state, and thereby a peripheral area in which the subject is not captured appears around the X-ray image created based on the X-ray transmission information, the area of interest is set in the peripheral area of the X-ray image.

4. The X-ray diagnostic apparatus according to claim 2, wherein in a case where the X-ray is transmitted through the subject in a narrowed state, and thereby a peripheral area in which the subject is not captured appears around the X-ray image created based on the X-ray transmission information, the area of interest is set in the peripheral area of the X-ray image.

5. The X-ray diagnostic apparatus according to claim 1, wherein the luminance-level-value computation unit calculates the amount of X-ray irradiation of the detector by using a relational expression representing a relation between the amount of X-ray irradiation and the output value.

6. The X-ray diagnostic apparatus according to claim 5, wherein the luminance-level-value computation unit calculates the amount of X-ray irradiation of the detector by taking into consideration a condition of the irradiation of the X ray to the subject.

7. The X-ray diagnostic apparatus according to claim 1, further comprising a notification unit configured to notify a result of the judgment by the end-of-life judgment unit.

8. The X-ray diagnostic apparatus according to claim 2, further comprising a notification unit configured to notify a result of the judgment by the end-of-life judgment unit.

9. The X-ray diagnostic apparatus according to claim 3, further comprising a notification unit configured to notify a result of the judgment by the end-of-life judgment unit.

10. The X-ray diagnostic apparatus according to claim 4, further comprising a notification unit configured to notify a result of the judgment by the end-of-life judgment unit.

11. The X-ray diagnostic apparatus according to claim 5, further comprising a notification unit configured to notify a result of the judgment by the end-of-life judgment unit.

12. The X-ray diagnostic apparatus according to claim 6, further comprising a notification unit configured to notify a result of the judgment by the end-of-life judgment unit.

13. The X-ray diagnostic apparatus according to claim 1, further comprising:
a communication control unit configured to enable a communication with an outside of the X-ray diagnostic apparatus, wherein
the result of the judgment by the end-of-life judgment unit is notifiable to the outside.

14. The X-ray diagnostic apparatus according to claim 2, further comprising:
a communication control unit configured to enable a communication with an outside of the X-ray diagnostic apparatus, wherein
the result of the judgment by the end-of-life judgment unit is notifiable to the outside.

15. The X-ray diagnostic apparatus according to claim 3, further comprising:
a communication control unit configured to enable a communication with an outside of the X-ray diagnostic apparatus, wherein
the result of the judgment by the end-of-life judgment unit is notifiable to the outside.

16. The X-ray diagnostic apparatus according to claim 5, further comprising:
a communication control unit configured to enable a communication with an outside of the X-ray diagnostic apparatus, wherein
the result of the judgment by the end-of-life judgment unit is notifiable to the outside.

17. The X-ray diagnostic apparatus according to claim 6, further comprising:
a communication control unit configured to enable a communication with an outside of the X-ray diagnostic apparatus, wherein
the result of the judgment by the end-of-life judgment unit is notifiable to the outside.

18. The X-ray diagnostic apparatus according to claim 7, further comprising:
a communication control unit configured to enable a communication with an outside of the X-ray diagnostic apparatus, wherein
the result of the judgment by the end-of-life judgment unit is notifiable to the outside.

19. An X-ray diagnostic apparatus comprising:
an X-ray generation unit configured to generate an X ray with which a subject is to be irradiated;
an X-ray detection unit including a detector and configured to create X-ray transmission information, the detector being configured to detect the X-ray transmitted through the subject;
an image creation unit configured to create an X-ray image on the basis of the X-ray transmission information; and
an end-of-life detection unit configured to detect an end of life of the detector on the basis of a pixel value in the X-ray image, wherein the end-of-life detection unit includes
- a luminance-level-value computation unit configured to calculate the pixel value in an area of interest which is set on any one of the X-ray image and the detector,
- a pixel-value accumulation unit configured to calculate an accumulated pixel value in the area of interest by adding the pixel value calculated by the luminance-level-value computation unit to a previous pixel value in the area of interest, and
- an end-of-life judgment unit configured to make a judgment on the end of life of the detector on the basis of the accumulated pixel value.

20. An X-ray diagnostic apparatus comprising:
an X-ray generation device including
- an X-ray generation unit configured to generate an X ray with which a subject is to be irradiated, and
- a system control unit configured to control the X-ray generation unit; and an image collection device including
- an X-ray detection unit including a detector and configured to create X-ray transmission information, the detector being configured to detect the X ray transmitted through the subject,
- an image creation unit configured to create an X-ray image on the basis of the X-ray transmission information,
- a luminance-level-value computation unit configured to calculate an amount of X-ray irradiation of the detector on the basis of the output value in an area of interest which is set on any one of the X-ray image and the detector,
- an irradiation-amount accumulation unit configured to calculate an accumulated amount of irradiation in the area of interest by adding the amount of X-ray irradiation calculated by the luminance-level-value computation unit to a previous amount of X-ray irradiation in the area of interest, and
- an end-of-life judgment unit configured to make a judgment on an end of life of the detector on the basis of the accumulated amount of irradiation.

* * * * *